United States Patent
Chadri et al.

(10) Patent No.: US 11,977,029 B2
(45) Date of Patent: May 7, 2024

(54) OFFSET RAMAN IMAGING SYSTEM AND METHODS OF USE

(71) Applicant: Dawatek, LLC, Oak Park, IL (US)

(72) Inventors: Isaac W. Chadri, Oak Park, IL (US); Edward Guen-Murray, Chicago, IL (US)

(73) Assignee: Dawatek, LLC, Oak Park, IL (US)

( * ) Notice: Subject to any disclaimer, the term of this patent is extended or adjusted under 35 U.S.C. 154(b) by 296 days.

(21) Appl. No.: 17/480,681

(22) Filed: Sep. 21, 2021

(65) Prior Publication Data

US 2022/0003680 A1 Jan. 6, 2022

Related U.S. Application Data

(63) Continuation of application No. PCT/US2020/023991, filed on Mar. 20, 2020.

(60) Provisional application No. 62/821,562, filed on Mar. 21, 2019.

(51) Int. Cl.
*G01J 3/44* (2006.01)
*G01N 21/65* (2006.01)

(52) U.S. Cl.
CPC .............. *G01N 21/65* (2013.01); *G01J 3/44* (2013.01); *G01N 2201/06113* (2013.01)

(58) Field of Classification Search
CPC . G01N 21/65; G01N 2201/06113; G01J 3/44; G01J 3/0272; G01J 3/10; G01J 3/0218; A61B 5/0075; A61B 2505/05
See application file for complete search history.

(56) References Cited

U.S. PATENT DOCUMENTS

| | | | | |
|---|---|---|---|---|
| 4,443,684 A | * | 4/1984 | Sakuragi | B23K 26/034 219/121.81 |
| 5,575,936 A | * | 11/1996 | Goldfarb | B23K 26/0869 219/121.61 |
| 5,801,666 A | * | 9/1998 | MacFarlane | G09F 19/12 348/E13.059 |
| 2003/0052105 A1 | * | 3/2003 | Nagano | B29C 64/277 219/121.83 |
| 2004/0051777 A1 | * | 3/2004 | Miller | B23K 26/066 347/224 |
| 2010/0172020 A1 | * | 7/2010 | Price | G02B 21/244 359/383 |
| 2011/0298800 A1 | * | 12/2011 | Schlichte | G06T 15/04 345/420 |
| 2014/0377874 A1 | * | 12/2014 | Jahnen-Dechent | G01N 33/6893 436/34 |

* cited by examiner

*Primary Examiner* — Abdullahi Nur
(74) *Attorney, Agent, or Firm* — J. Peter Paredes; Amin Talati Wasserman LLP

(57) ABSTRACT

An Offset Raman imaging device and methods of use is disclosed and generally comprises a Raman laser and a XY plotter, wherein the Raman laser and the XY plotter are operably coupled to take Raman spectra scans of a region of interest.

10 Claims, 11 Drawing Sheets

US 11,977,029 B2

OFFSET RAMAN IMAGING SYSTEM AND METHODS OF USE

BACKGROUND

The present application claims priority to PCT application serial no. PCT/US2020/023991, filed Mar. 20, 2020, which claims priority to U.S. provisional application Ser. No. 62/821,562, filed Mar. 21, 2019, all herein incorporated by reference in entireties.

Raman spectroscopy is the study of small shifts in the Wavelength of photons, usually generated by a laser, as the photons undergo inelastic Raman scattering with molecules in various media. Interaction With different molecules gives rise to different spectral shifts, so that analysis of a Raman spectrum can be used to determine chemical composition of a sample. The very Weak nature of the scattering makes Raman spectroscopy difficult to use in many circumstances, due to the Raman signal being swamped by fluorescence and other background signals.

Raman spectroscopy on its own isn't good enough to scan tissue samples at great depths, and that is because the vibrational frequencies get absorbed by surrounding tissue thus reducing the signal and making it inaccurate.

The present invention attempts to solve these problems as well as others.

SUMMARY OF THE INVENTION

Provided herein are systems, methods and compositions for an offset Raman imaging system and methods of use.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

Figure 1A:
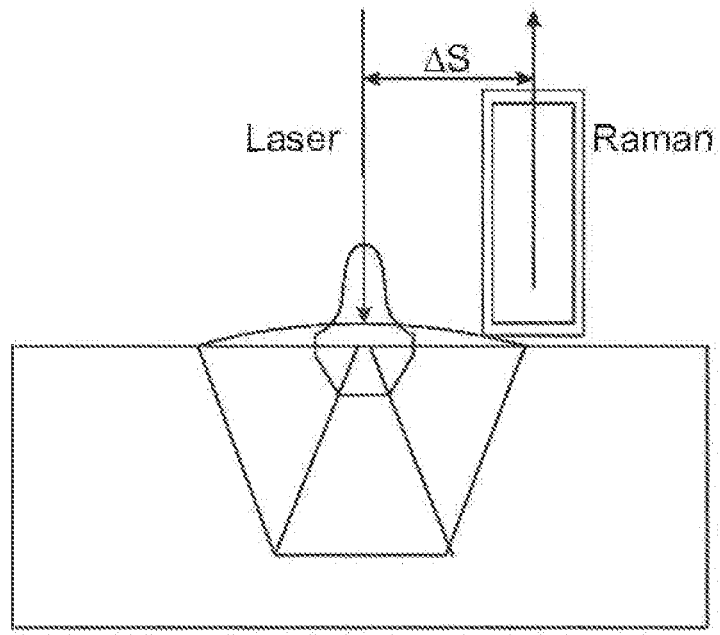
FIG. 1a is a schematic diagram of the principal of spatially offset Raman spectroscopy.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Generally speaking, the Offset Raman imaging device comprises at least two separate and modified components including a Raman laser and a XY plotter, wherein the Raman laser and the XY plotter are operably coupled to take Raman spectra scans of a region of interest (ROI) and to convert the Raman spectra scans into grayscale 2D and 3D images of the ROI. Raman Spectroscopy is a form of molecular analysis that is in the same wavelength range as IR, and it works by picking up the vibrational frequencies and other low-frequency nodes in a system. The incident light excites molecular vibrations in the system adding to a shift of the scattered light which is analyzed. Thus, the Raman spectrum is fundamentally a vibrational spectrum and may be regarded as a "fingerprint" of the scattering material providing qualitative and quantitative information about the molecular composition and structure (Li-Chan, Griffith, & Chalmers, 2010; Schmidt, Scheier, & Hopkins, 2013). The principal of Raman spectroscopy is shown in FIG. 1a.

Figure 1B:
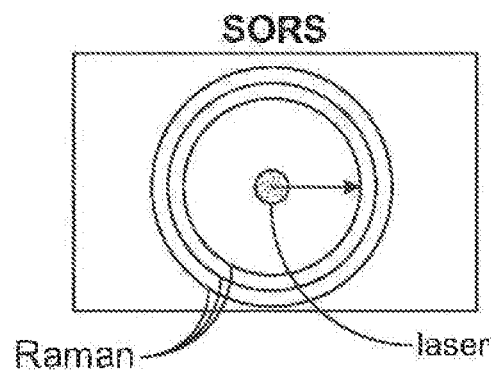
FIG. 1b is a schematic diagram of conventional SORS showing Raman collection and beam delivery geometries.
Figure 1C:
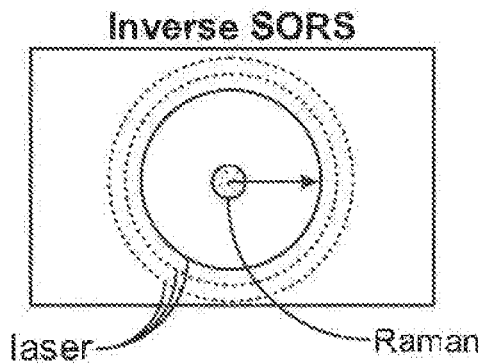
FIG. 1c is a schematic diagram of inverse SORS showing Raman collection and beam delivery geometries.

A schematic diagram of conventional Spatially-Offset Raman Spectroscopy (SORS) is shown in FIG. 1b. The principal of the SORS technique is based on collecting a set of Raman spectra from the surface regions of a sample that are at set distances, Δs, away from the point of illumination by the laser. Raman spectra obtained in this way exhibit a variation in relative intensities between the contributions from the surface and sub-surface layers. Such a set of spectra can be numerically processed to yield the pure Raman spectra of individual sub-layers. Inverse SORS showing Raman collection and beam delivery geometries is shown in FIG. 1c. In inverse SORS, Raman light is collected through a group of fibers tightly packed at the center of the probe by binning all their signals on CCD chip into a single spectrum. The fibers can be randomly organized as is often the case with commercial fiber probes. The laser probe beam is brought onto the sample in the form of ring of a given radius centered at the collection zone, i.e. in reverse to conventional SORS (see FIG. 1c). The artefact problems are absent as all Raman spectra are subject to the same imaging distortions and collected through the same set of CCD pixels.

Figure 4A:
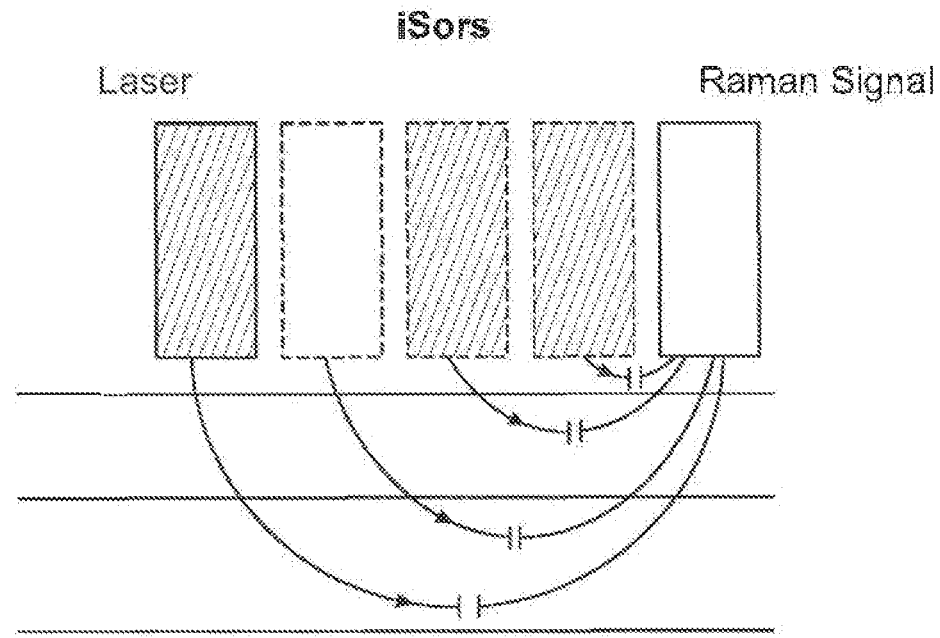
FIG. 4a is a schematic diagram of iSORS.
Figure 4B:
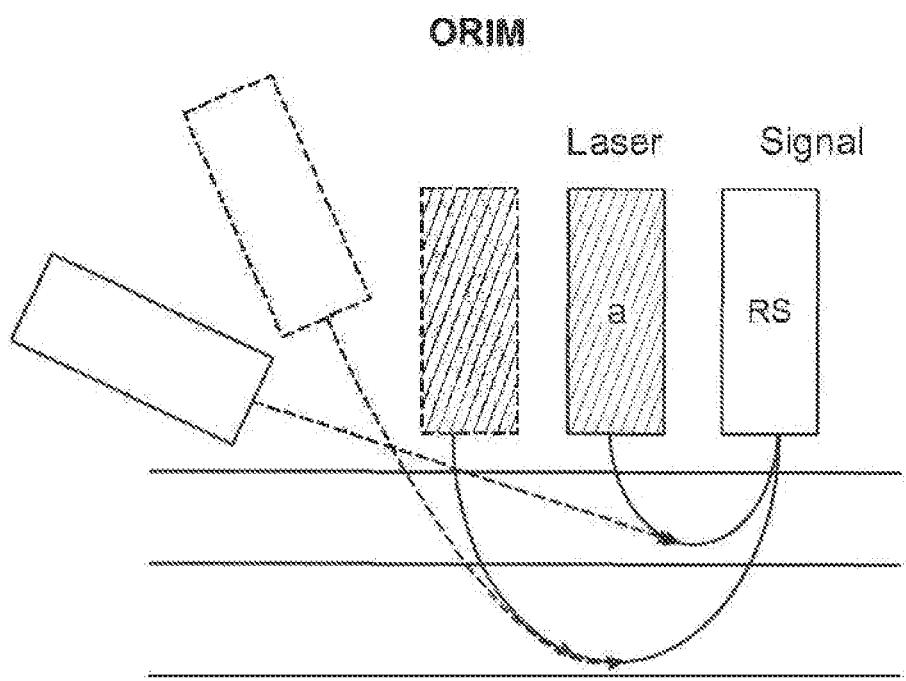
FIG. 4b is a schematic diagram of ORIM.
Figure 4C:
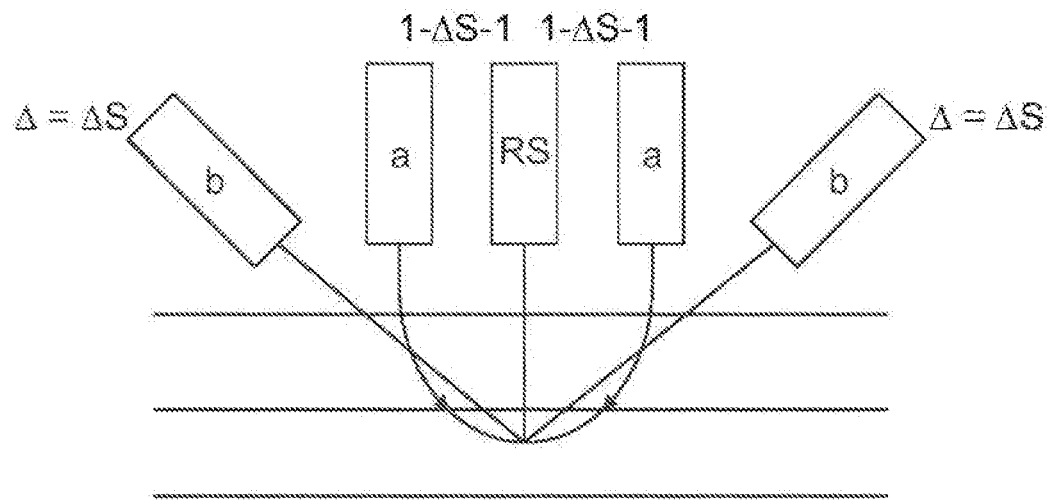
FIG. 4c is a schematic diagram of one embodiment of the probe of the laser including a second ring of laser fibers at an angular incidence that expands and contracts with the original ring of laser fibers.
Figure 4D:
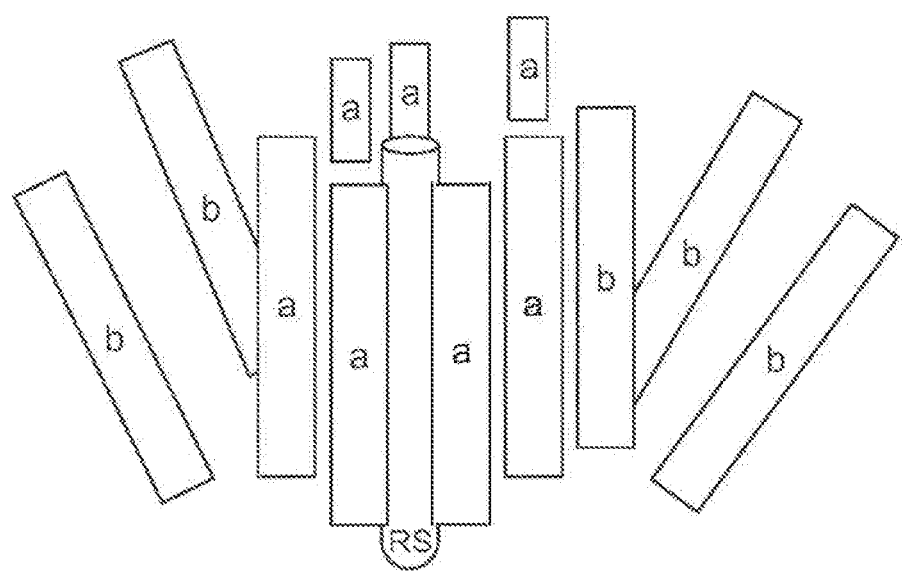
FIG. 4d is a schematic diagram of one embodiment of the probe of the laser including a plurality of probes.

As shown in FIGS. 4a-4b, the laser component of the device is comprised of an Inverse Spatially Offset Raman Spectroscopy system (iSORS) with additional modifications. The laser component includes a probe, which includes a second ring b (FIG. 4c) including a plurality of lasers fibres at an angular incidence that expands and contracts with the original ring of laser fibres (FIG. 4b). This is done by having both rings expand proportional to the movement of the axicon (image of axicon with iSORS). As the second ring expands and contracts, the angle of incidence decreases and increases, respectively (FIGS. 4b-4c). The addition of the second angled ring of lasers would provide greater intensity of the Raman signal, because the path travelled by both rings of lasers would converge on the same spot, giving a stronger signal and thus allowing it to probe deeper into tissue samples.

Figure 5A:
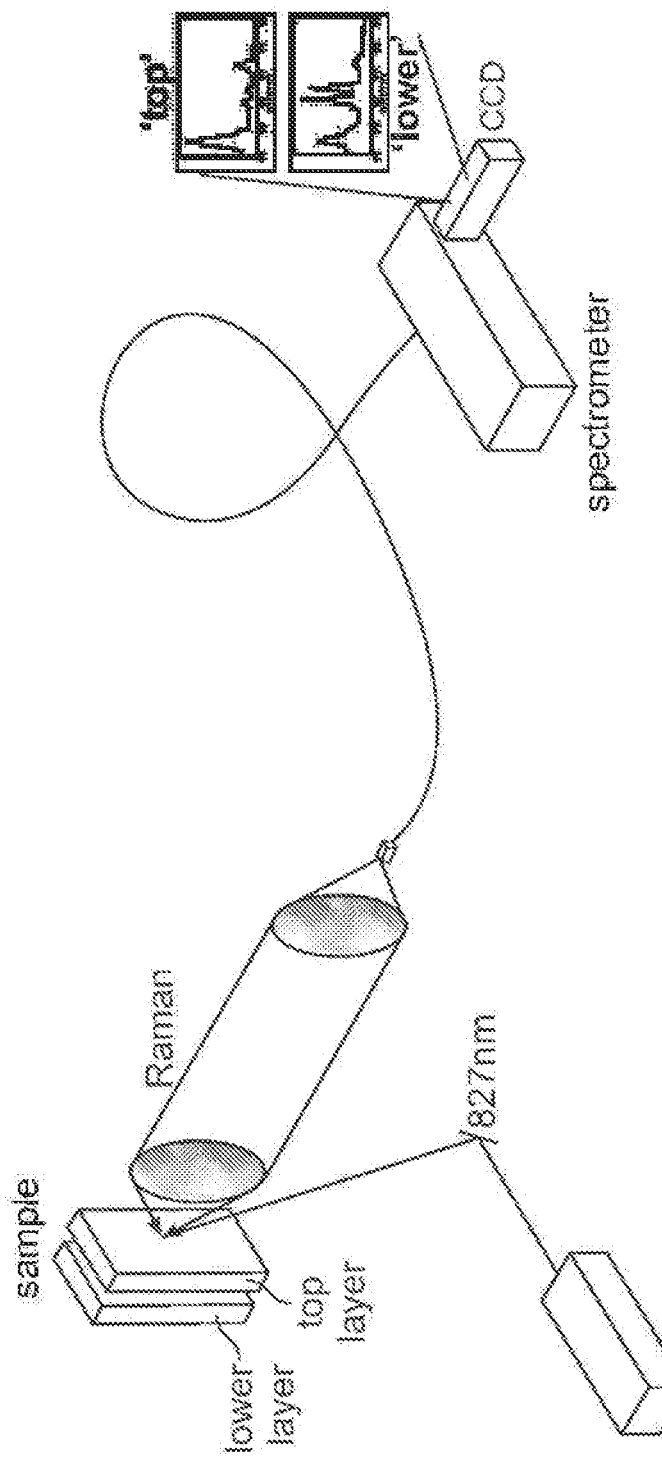
FIG. 5a is a schematic diagram of the SORS system.

The iSORS system is generally shown in FIG. 5a. The experiments were performed using a temperature stabilized diode laser for Raman spectroscopy operating at 827 nm with a laser beam power at the sample of 50 mW. The collimated beam of 3 mm diameter was passed through a UV fused silica axicon element with a cone angle a=5° (DelMar Ventures) placed on a rail to permit the sample to axicon distance to be varied in the range 60 to 155 mm (corresponding to the spatial offsets from 0.9 to 7.9 mm). The zero radius (conventional Raman geometry) was realized by physically removing the axicon from the beam. For practical reasons, the transmitted part of the beam was incident on the sample at ~45° degrees away from normal incidence. Raman light was collected in backscattering geometry using a 50 mm diameter lens with a focal length of 60 mm. The scattered light was collimated and passed through a 50 mm diameter holographic notch filter (830 nm, Kaiser Optical Systems, Inc.) to suppress the elastically scattered component of light. The second lens, identical to the first one, was then used to image, with magnification 1:1, the sample interaction zone onto the front face of the annular fiber probe. The Raman light was propagated through the SORS annular fiber systems of length ~2 m to the linear fiber end oriented vertically and placed in the input image plane of a Kaiser Optical Technologies Holospec f#=1.4 NIR spectrograph with its slit removed. Raman spectra were collected using a NIR back-illuminated deepdepletion TE cooled CCD camera (Andor Technology, DU420A-BR-DD, 1024× 256 pixels). The light collection end of the inverse SORS fiber probe was constructed with 61 fibers tightly packed at the center of the probe although only 22 fibers within the center of the probe could be coupled to the detector due to physical constraints stemming from the height of CCD chip. The individual fibers were made of silica with a core diameter of 220 μm. The fiber numerical aperture was 0.37. The bundle was custom made by CeramOptec Industries, Inc. The comparative conventional SORS experiments presented here were performed using a two-track SORS fiber prob. In these measurements the laser power was around 80 mW at the sample and the laser beam was focused down to 0.2 mm diameter spot. The SORS probe had 7 and 26 fibres for the zero and 3 mm spatial offset tracks, respectively. The fibers had a core diameter of 200 μm and a numerical aperture of 0.37.

The laser component is further comprised of iSORS with a frequency-offset Raman spectroscopy (FORS) system. FORS is when Raman spectroscopy is performed at different excitation frequencies which make it possible to selectively probe different parts of the medium, provided that different optical properties versus frequency are observed (Sekar et. al., 2017).

When experimented on tissue phantoms, the hybrid FORS-SORS technique had an enhancement of 6.0, which is higher than for SORS alone (2.62) or FORS alone (2.81) (Sekar et al., 2017). Doing this just requires changing the frequency based on the optical properties of the tissue. After gathering spectra of every type of tissue, the software would work with the Raman Spectroscopy software to change the frequency, as further detailed below.

Figure 5B:
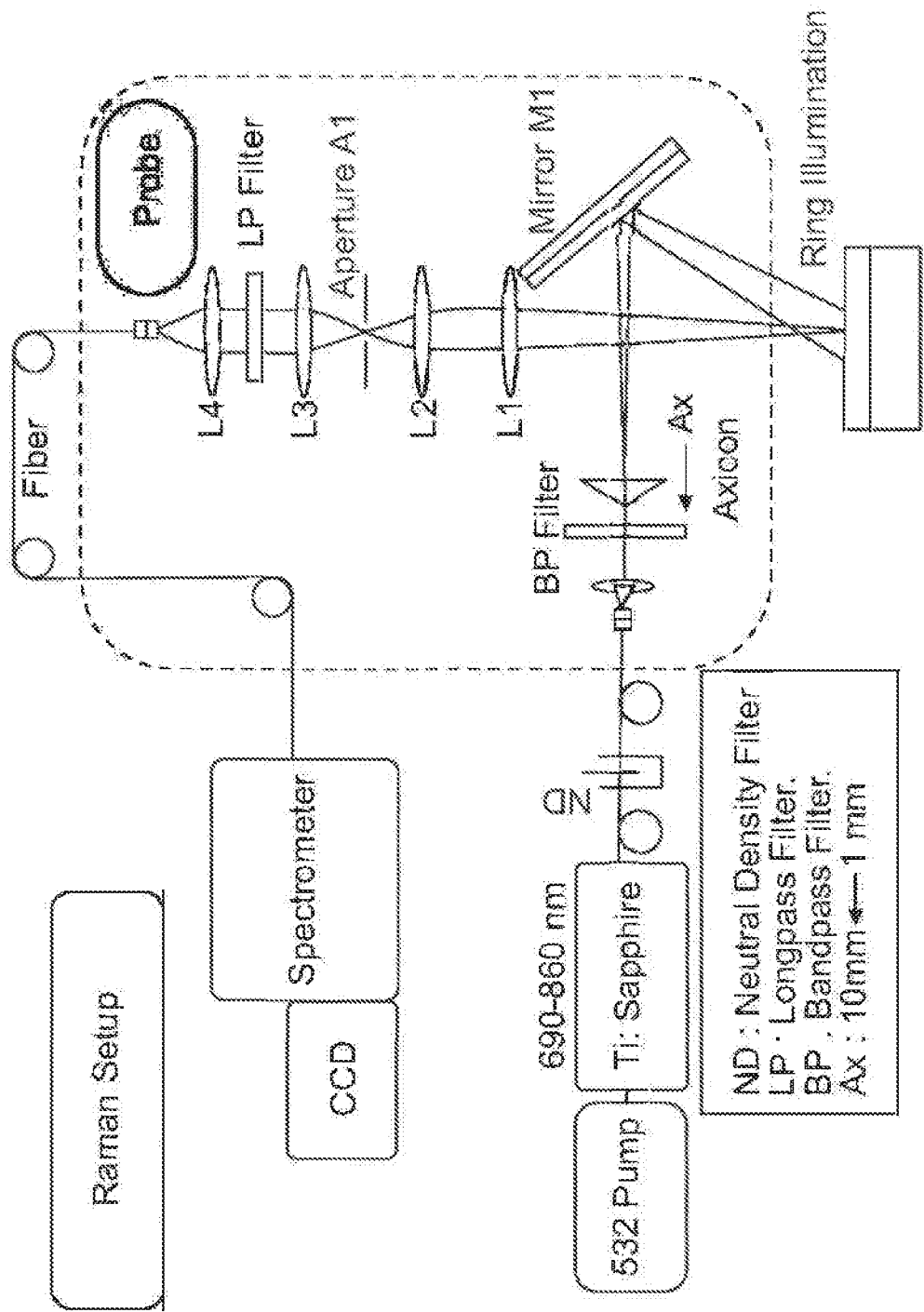
FIG. 5b is a schematic diagram of the setup for SORS and FORS system.

In one embodiment, the FORS system is shown in FIG. 5b. A Ti:Sapphire laser pumped by 532 nm light from a frequency doubled Nd:YAG laser provides a tunable laser source in the 690-860 nm range. A 100 μm optical fiber couples the light from the laser to a collimator in the Raman probe, built using Thorlabs 30 mm diameter cage system. Depending on the excitation wavelength, a suitable 10 nm bandwidth bandpass filter (700 nm, 750 nm, 780 nm, 810 nm) is used to clean the laser beam. An Axicon lens (UV fused silica axicon element with a cone angle $\alpha=5°$) is then exploited to create ring illumination. Mirror M1 (silver mirror) reflects the ring source onto the sample. The radius of the ring illumination can be varied from 1 mm to 10 mm by moving the Axicon on its railing away from mirror M1. Cross positioning of mirror M1 and the corresponding incidence direction, slightly tilted with respect to normal incidence, distort only negligibly the shape of the ring. The source-detector separation d is calculated between the center of point collection and the inner radius of ring illumination. The collection system involves a set of four optical lenses (diameter 25 mm) with effective f-number f/2. L2 and L3 along with a narrow aperture (A1) act as a Fourier optical low pass filter system, which enhances point collection and prevents stray light from entering the detection system. A suitable long pass filter (715 nm, 750 nm, 785 nm, 808 nm) is placed between lenses L3 and L4 to remove the excitation photons effectively. L4 couples the Raman signal into a 1 mm optical fiber, which transfers the light to a spectrometer (Acton SpectraPro2150, Princeton Instruments, f/4 system, grating 1200 grooves/mm) through a 200 μm slit. A cooled CCD camera (iDUS DV401A, Andor Technology Ltd., 1024×255, pixel size 26×26 μm2) is used to record Raman spectra. The CCD is vertically binned to increase signal intensity, while maintaining spectral resolution.

Another embodiment of the laser is the addition of a diode sheet at the collection end of the probe with a hole in the middle. The diode sheet reflects scattering signals back into the tissue and gives the spectrometer a better signal by x1.2-2.3 (Matousek et al. Development of Transmission Raman Spectroscopy towards the in line, high throughput and non-destructive quantitative analysis of pharmaceutical solid oral dose, Analyst, 2015,140, 107-112). The effects of the diode rely on how close the tissue sample is to the diode sheet and the tissue type, and this is because this was reported to be used at a depth of 10 mm.

Figure 2A:
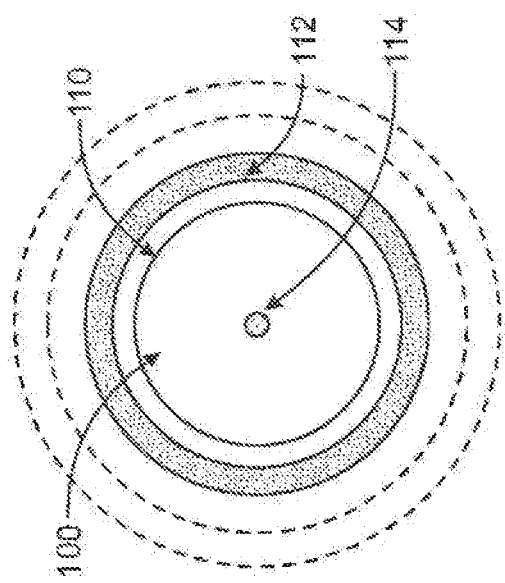
FIG. 2a is a diode sheet with a first ring of lasers and a second ring of lasers and the Raman collection end in the middle.

As shown in FIG. 2a, the diode sheet 100 includes a first ring of lasers 110, a second ring of lasers 112 surrounding the first ring of lasers 110 and a Raman collection end 114 in the middle of the first ring of lasers 110 and the second ring of lasers 112. A space 116 without the diode sheet is between the Raman collection end 114 and the first ring of lasers 112.

Figure 2B:
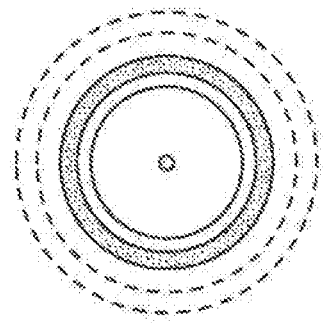
FIG. 2b is a diode sheet with a hole in the middle.
Figure 2B:
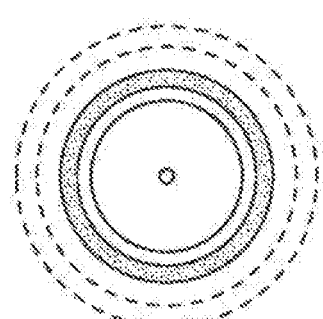
Figure 2B:
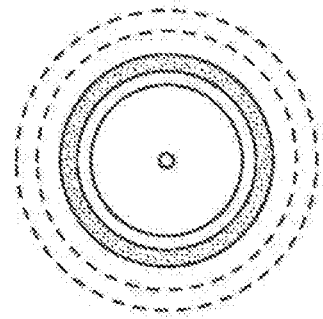
Figure 2B:
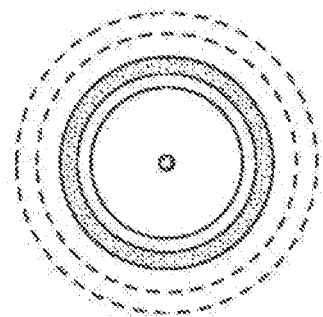
Figure 3A:
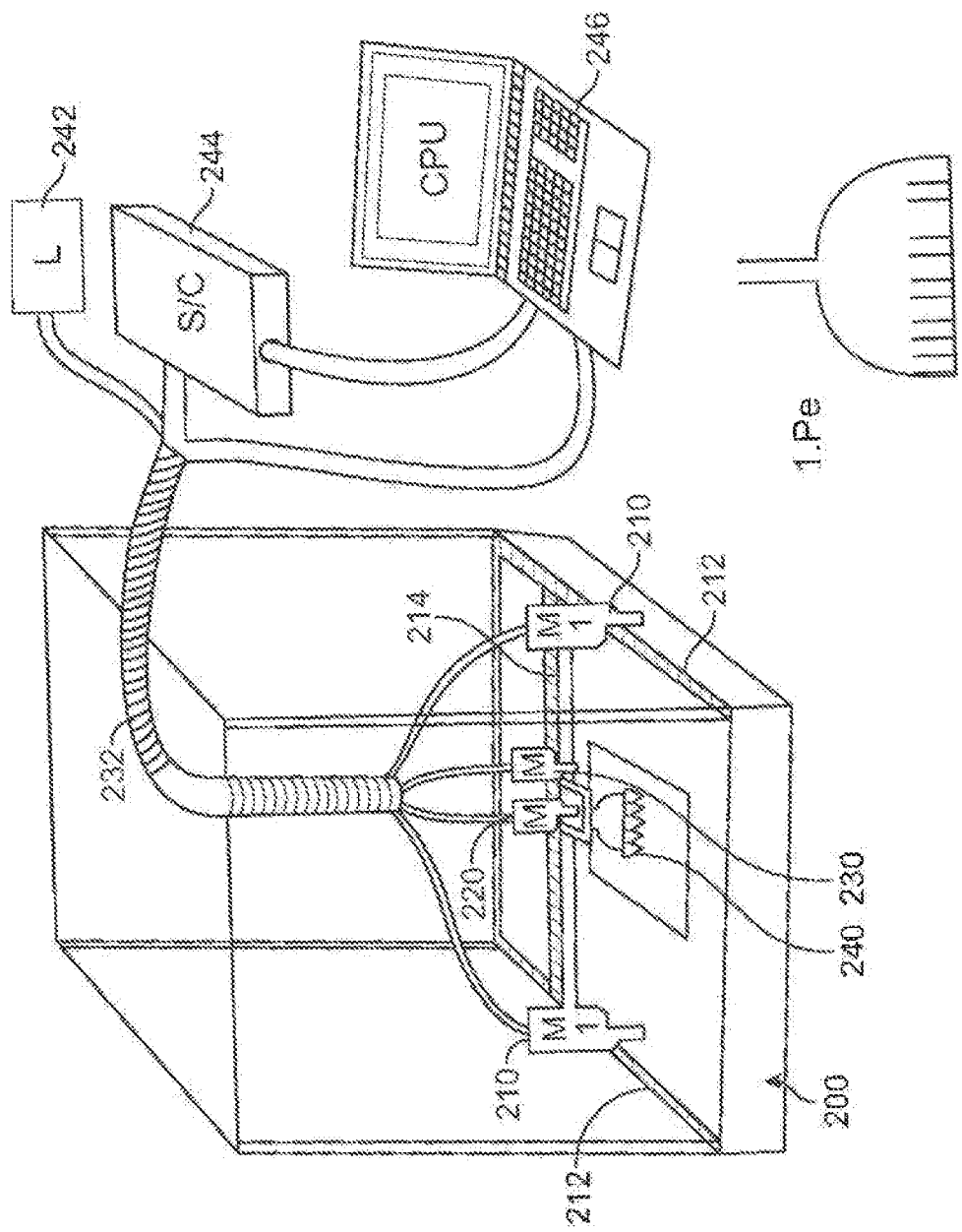
FIG. 3a is a perspective view of a schematic diagram of the XY plotter.

One embodiment of the probe is shown in FIG. 3a. Another embodiment of the probe may include a plurality of laser figures lined up side by side, so that the machine can just move in one direction and have one size, as shown in FIG. 2b.

In one embodiment, this technique may be used for chemical analysis and identification, since it could tell you the chemical "fingerprint" of whatever you scanned. Then Raman started being applied first in pharmaceutical companies to scan products and eliminate "knock off" medicine (Ricci et al., 2007), then secondly with airport security using the same process as pharmaceutical companies, but to detect harmful/explosive substances.

Then because of Raman's ability to get the chemical "fingerprint" of anything it scans, it may be used on human bones for abnormal bone composition measurement, bone disease diagnosis (Matousek and Stone, 2013; Buckley et al., 2014). In one embodiment, cancer detection may be employed by Raman using SERS (Surface Enhanced Raman Spectroscopy), Transmission Raman, SESORS (Surface-Enhanced Spatially-Offset Raman Spectroscopy) and they have been paired with nanoparticles and quantum dots (Matousek and Stone, 2013; Qian et al., 2007; Paciotti et al., 2004).

The key difference between all these previous techniques and models is that they all aim to detect cancer/abnormalities if the location and type is already known. They are all scanning tissues/bones to detect the spectra for cancer then label it as such. The end result is a spectra having the assigned peaks for cancer. Prior to scanning, the offset Raman imaging method obtains a library of all tissue and disease spectra, choosing to read every single spectra of each tissue/abnormality in the Region of Interest (ROI), spatially map out where each spectra is in relation to the tissue, match each spectra to one in the library, then produce a grayscale image of the ROI which would show and identify any abnormality. This would be possible because Raman provides the chemical "fingerprint" of what is scanned, so every single tissue (fat, muscle, connective, bone, different types of cancer) would have its own chemical "fingerprint" that can be identified on the image with ease.

The offset Raman imaging method comprises several different types of Raman Spectroscopy so as to amplify the Power of the laser. The offset Raman imaging method comprises iSORS, and comprises an extra ring of lasers, then adding FORS and a diode sheet to the process. In Sekar et al., they created FORS and performed an experiment using a FORS-SORS hybrid which had a much greater penetration depth and cleaner signal (Sekar et al., 2017).

The advantages the offset Raman imaging method over current imaging modalities (MRI, CAT, X-RAY) are that there is no radiation emitted (X-Rays and CAT scans do so), it can scan both tissue and bone simultaneously, and that due to the cheap manufacturing cost, it becomes significantly cheaper for hospitals to buy which then makes it more affordable for patients. Another advantage is that since this can become a diagnostic medical device, it can eliminate the need to do a biopsy to find out what the abnormality is since the device would know its chemical signature.

Figure 3B:
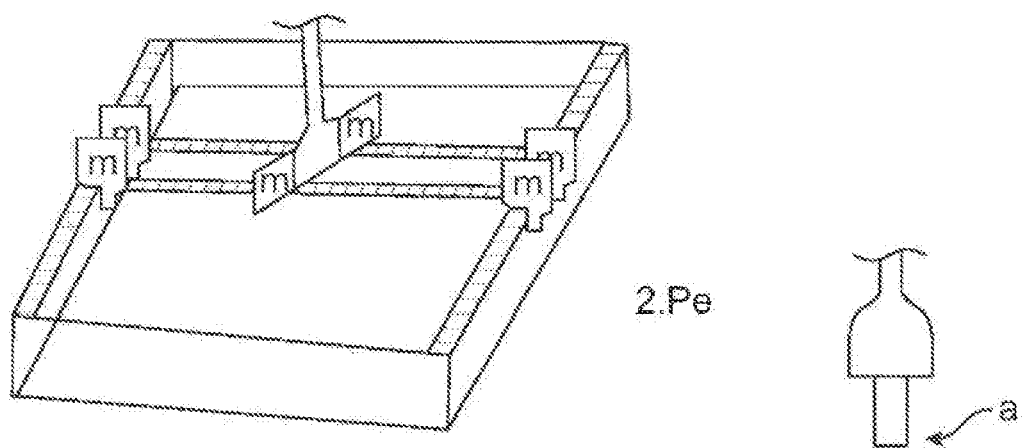
FIG. 3b is an enlarged perspective view of the XY plotter.
Figure 3C:
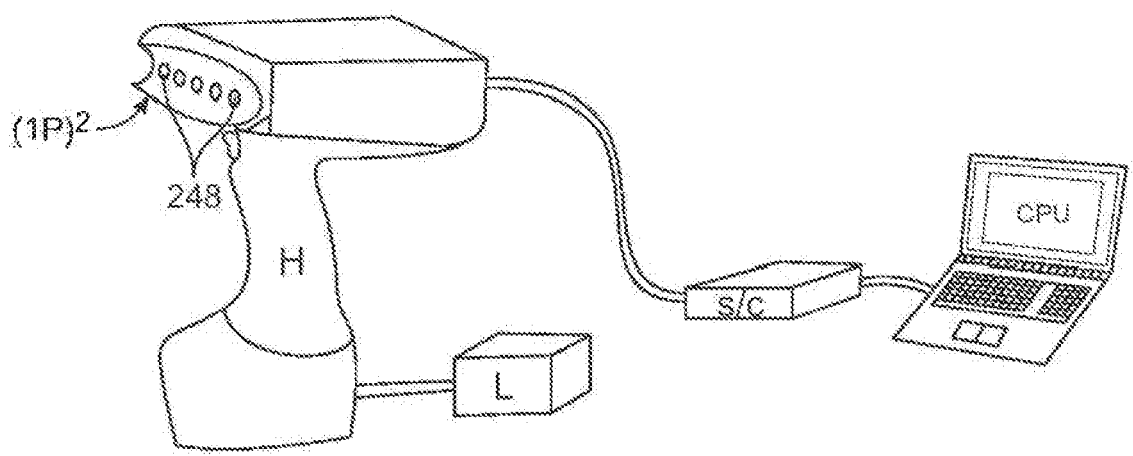
FIG. 3c is a perspective view of the probe operably coupled to the computer.

The offset Raman imaging method includes several modifications with the entire system, but they will mainly be within the robot and the software. With the robot, we plan on developing a handheld version of the device, which would use the same probe we designed (FIG. 3a and FIG. 2b) and would be able to be controlled by the user and applied on different parts of the body. The other thing that might change is that the probe may go from being 5 in-a-row and diffract into a 5×5 grid of probes (FIG. 3c)

In one embodiment, the software module is subject to change including but not limited the following: choosing at least 5 or 6 peaks that characterize tissue (5 or 6 cells excel sheet); in case the actual data proves to be too much (500-2000 data points); addition of PLS and Normalization to graphs.

XY Plotter:

The XY plotter controls the movement of the probe with a plurality of motors and a plurality of sensors to actively communicate with the XY plotter regarding the probe's distance from the sample. The plurality of motors and the plurality of sensors communicate data regarding how far away probe is from the sample being scanned. In one embodiment, the XY plotter 200 as shown in FIG. 3a-3c, comprises at least 2 motors (210) sitting on each vertical track (212) at the end of the horizontal track (214). The second motor (220) would move the probe left to right, while the third motor (230) would move the probe (240) up and down and attached to it is a sensor which tells the plotter how far it is from the sample. This sensor has to be touching the skin for Raman Spectroscopy and any version of it, and this allows the machine to maintain 1 cm distance from the sample while moving. In one embodiment, the plotter will be encased in glass with steel rods at the corners so that it stabilizes plotter while it's moving. The cables 232 for all the motors and probe will be bundled together with enough slack so that the plotter can move freely, and the bundled cables will pass through the encasing then split out to the laser source (242), the spectrograph/CCD camera (244) then a CPU/computer (246). In one embodiment, the probe (FIG. 3c) includes at least 5 individual probes 248, as stated above.

In one embodiment, there is adequate signal strength for clinical applications, the sensitivity and penetration depth of the technique can be improved further by increasing the power of the incident light beam and the efficiency of the collection system. For example, the incident light beam and consequently the region of interest may be enlarged, for example to a diameter of several centimeters, allowing incident light beam powers approaching 1 Watt to be used safely. The collection optics may be similarly scaled to collect as much of the transmitted light as possible, for example using imaging optics, a large fiber bundle, or both to cover an large second surface region. The probe and collection optics can take a variety of forms. The illumination light may be projected onto the region of interest from wide range of distances, depending on the detailed circumstances of the application, using imaging optics or optical fibers.

Although the invention has been principally described in relation to noninvasive in vivo clinical applications, essentially the same methods and apparatus using Raman spectroscopy in transmission geometry may be used to characterize in-vivo tissues during surgical or invasive procedures. Such procedures may be minimally invasive, for example by inserting just one of the probes or collection optics within an opening, for example under the skin, using a needle probe or similar.

With the method and apparatus of the present invention, substantially pure Raman spectra can be retrieved from depths well in excess of those accessible with conventional confocal microscopy. Moreover, the present invention has the advantage that it is compatible with the use of cW lasers beams and is suited to remote monitoring in both industrial and medical applications. Thus the method and apparatus are well suited to not only biomedical applications, where monitoring sub-surface tissue layers normally would require destroying surface tissue, but also many industrial analytical applications such as catalysts, food, and polymers research applications. The present invention may be used to detect contamination of food during manufacture or the deleterious breakdown of food in storage as Well as the stability of stored pharmaceuticals in all cases without any contact with the sample.

Handheld Prototype

Figure 6A:
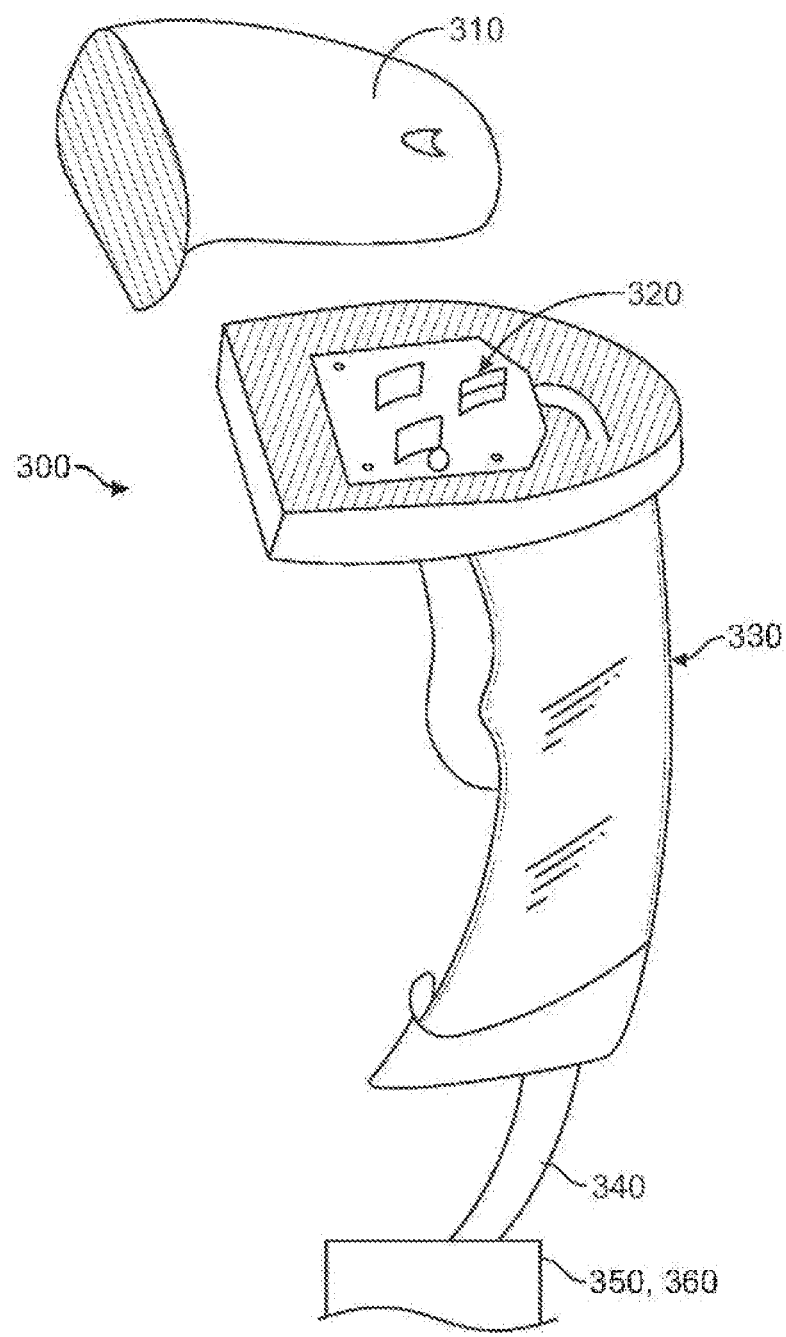
FIG. 6a is a schematic diagram of a second embodiment of the Offset Raman Imaging Machine (ORIM) 300.
Figure 6B:
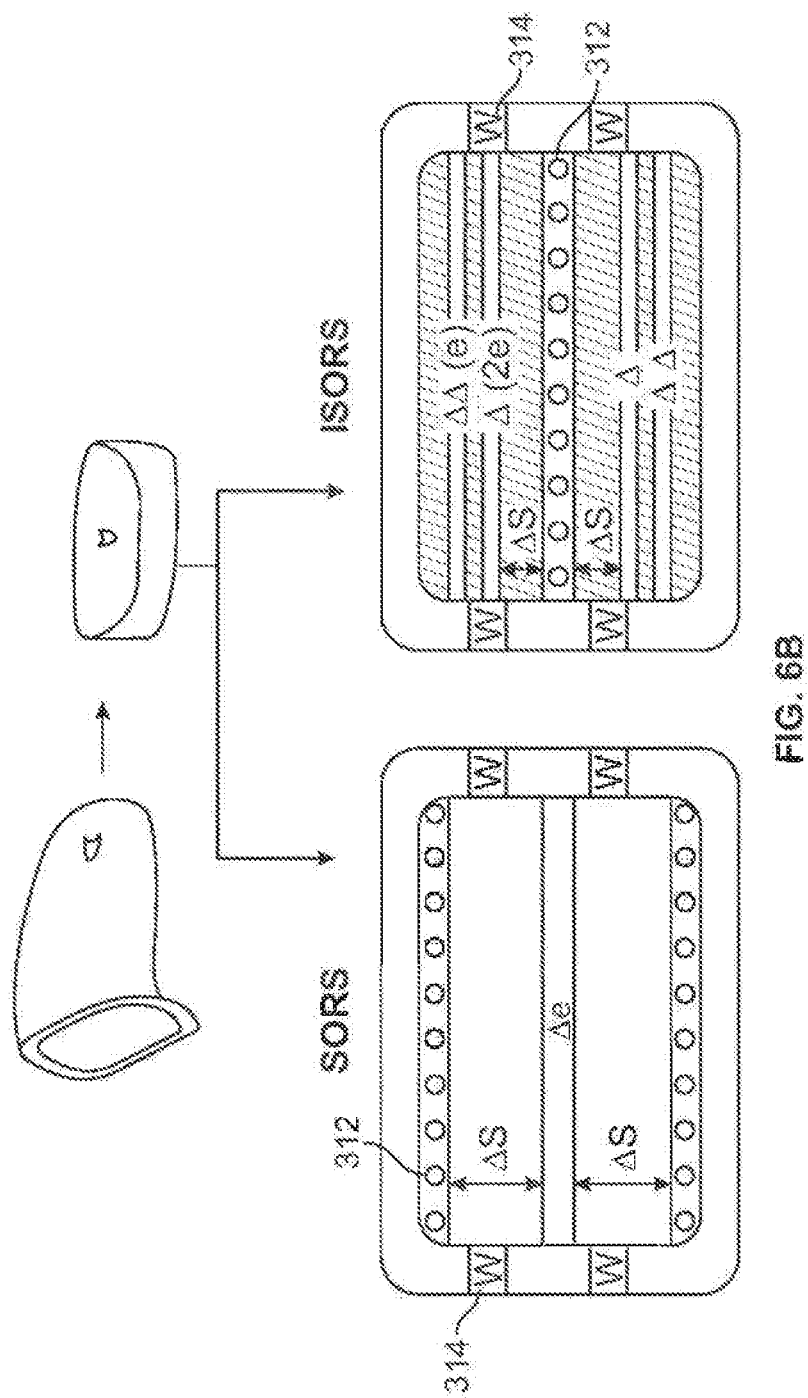
FIG. 6b is a schematic diagram of the handheld embodiment.
Figure 6C:
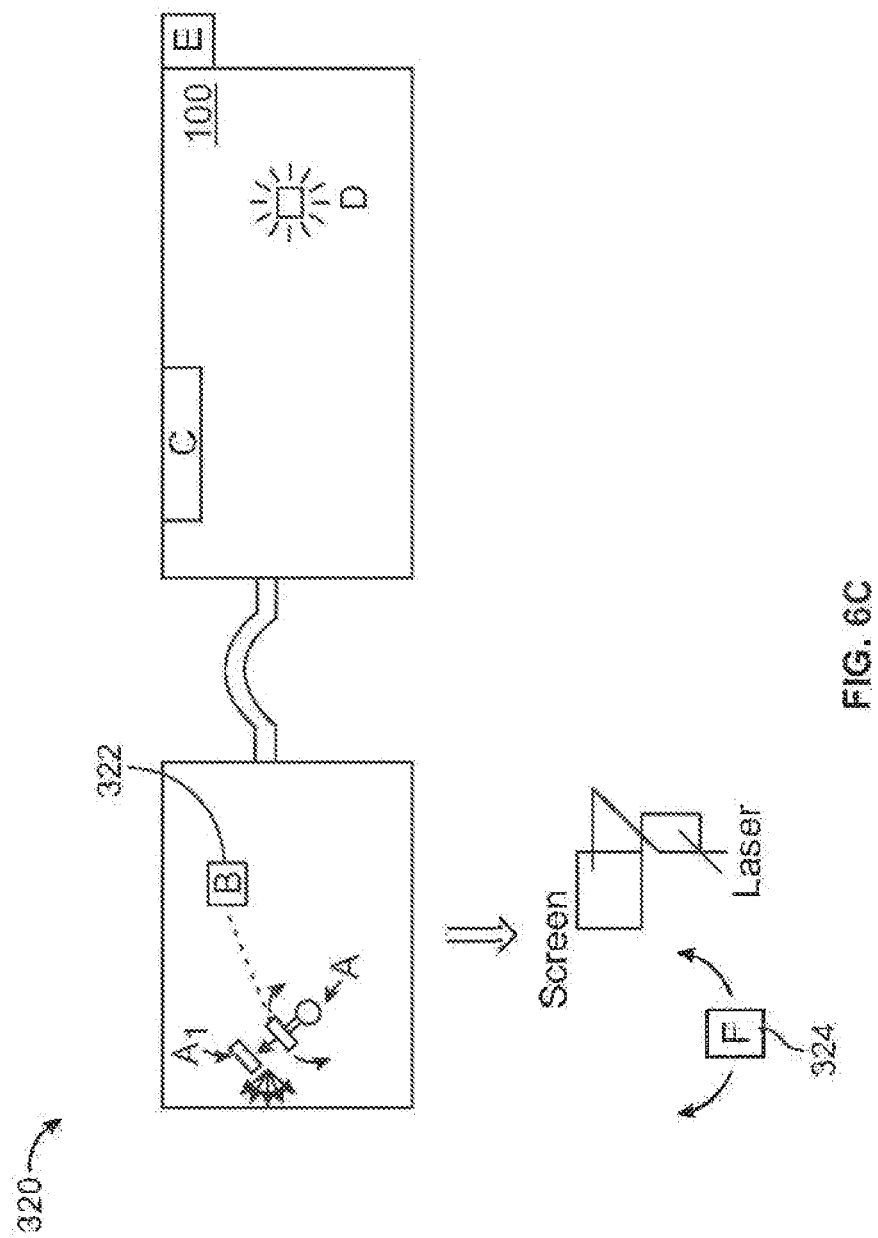
FIG. 6c is a schematic diagram of the circuit board.

As shown in FIGS. 6a-6c, the second embodiment of the Offset Raman Imaging Machine (ORIM) 300 scans areas of the body which have odd angles or near the head. It differs from the first prototype in how and where the fiber optic cables are placed in order to scan. The ORIM device 300 comprises a head 310 with a plurality of probes, a circuit board 320, a handheld frame 330, a fiber optic/USB bundle 340, a laser source 350, and a computer 360.

As shown in FIG. 6b, starting with head 310 with plurality of probes 312, this is how the fiber optics will be arranged on the screen of the device. There are two possible setups for the fiber optics, either SORS or iSORS. Both setups have (w) wheels 314 that are motorized, controlled by the circuit board (320) and can roll on the surface of the skin. This helps stabilize the device and control the speed of movement so that it moves at the correct rate the laser and spectrometer is taking readings. They also serve as vertical spatial markers to help the code keep track of where each scan is taken. For example, if the desired region of interest (ROI) is 10 cm×10 cm with a scan every 0.5 cm that takes 2 seconds per scan, and say it takes the wheels 20 rotations to go 10 cm. The programing would then tell the wheels to move every two seconds for 40 s.

As shown in FIG. 6b, the SORS setup a laser that is converted from a point to a horizontal axis line down the middle (l). At the top and bottom of the screen is a row of raman probes 312 (x) which move simultaneously according to the desired radius ($\Delta$s) that will be controlled by the circuit board (320). The Raman probes 312 opposite each other will collect the same information, average the spectra, and send the average to computer program, where now the code will then convert the spectra into a spatial image. The number of probes will serve as a horizontal spatial marker.

As shown in FIG. 6b, the iSORS setup is just the inverse of the SORS setup, only that there is a first (l) and second (2l) horizontal split laser line at the top and bottom of the screen. The two rows on the top and bottom of the screen will also move simultaneously according to the desired radius ($\Delta$s) and are controlled by the circuit board (320). Each raman probe in the middle will acquire a spectra and send to the computer where the program will convert it to a spatial image. Similar to the SORS probes, the iSORS probes serve as horizontal spatial markers.

As shown in FIG. 6c, the circuit board (320) is responsible for splitting the laser beam, controlling the shutter on the laser beam, and powering the device. To split the laser, it is attached to port B 322 which holds the laser in place, then the laser follows the pathway through two mirrors (A and A1) and then out to the screen in the form of a line. The mirrors convert the single beam to a line by the laser hit mirror A1 then reflecting to mirror A as it vibrates back and forth and that displaying on the screen as a line. The other possible laser pathways are shown in (324). Port B will have a shutter on it to stop the laser from being on all the time and controlled by the trigger (C). The computing chip (D) controls the motor speed, vibrational speed of mirror A1, and the power. Port (E) serves as the power source and it can be either a USB port that connects to the computer or a battery.

The fiber optic/USB bundle (340) then connects out of the handheld device and goes to the laser source and computer (360) like the previous embodiment.

In one embodiment, a mouthpiece attaches to the handheld Raman device.

Software Module

The purpose of the software module is to convert excel files into 2D and 3D images of grayscale. The setup generally includes a library with instructions to take a $1^{st}$ derivative from each spectra, storing each spectra data as a list with name of tissue, and creating a library with 'list' of tissues and each 'list' has a 'key'. The software module then takes files from folder one at a time and goes through each file doing the following: Math Adjustments including Normalize instructions and taking the derivative. The software module then compares new graph to library and if matches, assign letter; which assigns numeric value. For a basic diagnostic, the software module repeats for every spectra it finds in folder and arranges the 'list' (array) in matrix shape of choice. Then with each 'key' in the matrix, the software module then scales the value in a 0-1 scale which is used for black and white images. For cancer detection, the software module looks at the designated cell value in all the excel file, then the value is switched to a 0-1 scale. Every new value is now put in a list then resized to fit the matrix (dimensions of scanned area). The software module then converts the matrix to an image using an RGB multiplication tool.

Software Description

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOW (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. An Offset Raman imaging device comprising:
    a. a Raman laser and a XY plotter, wherein the Raman laser and the XY plotter are operably coupled to take Raman spectra scans of a region of interest and to convert the Raman spectra scans into grayscale 2D and 3D images of the region of interest.

2. The device of claim 1, wherein the Raman laser comprises an Inverse Spatially Offset Raman Spectroscopy system; and the Raman laser is operably coupled with a probe and the Raman laser includes an original ring of laser fibers within the probe.

3. The device of claim 2, wherein the probe includes a second ring including a plurality of lasers fibers at an angular incidence that expands and contracts with the original ring of laser fibers expand proportional to the movement of the axicon, and as the second ring expands and contracts, the angle of incidence decreases and increases, respectively.

4. The device of claim 3, wherein the second ring of lasers provide greater intensity of the Raman signal by converging the path travelled by both rings of lasers on the same spot, and giving a stronger signal and allowing Raman laser to probe deeper into the region of interest.

5. The device of claim 4, further comprising a frequency-offset Raman spectroscopy system with the Inverse Spatially Offset Raman Spectroscopy system, wherein the frequency-offset Raman spectroscopy system includes different excitation frequencies and changing the frequency based on the optical properties of the region of interest after gathering spectra of every type of tissue, the code would work with the Raman Spectroscopy software to change the frequency.

6. The device of claim 5, further comprising a diode sheet at the collection end of the probe with a hole in the middle, wherein the diode sheet reflects scattering signals back into the region of interest and provide a better signal for a spectrometer.

7. The device of claim 6, wherein the XY plotter controls the movement of the probe with a plurality of motors and a plurality of sensors to actively communicate with the XY plotter regarding the probe's distance from the region of interest.

8. The device of claim 7, wherein the plurality of motors and the plurality of sensors communicate data regarding how far away probe is from the region on interest being scanned.

9. The device of claim 8, wherein the plurality of motors comprise a first motor, a second motor, and a third motor; wherein the first motor is positioned on a vertical track and at the end of a horizontal track; the second motor moves the probe horizontally; the third motor moves the probe along a Z-axis; and a sensor operably coupled with the XY plotter to indicate how far the probe is away from the region of interest.

10. An Offset Raman imaging system comprising: a Raman laser and a XY plotter, wherein the Raman laser and the XY plotter are operably coupled to take Raman spectra scans of a region of interest and to convert the Raman spectra scans into grayscale 2D and 3D images of the region of interest; wherein the Raman laser comprises an Inverse Spatially Offset Raman Spectroscopy system; and the Raman laser is operably coupled with a probe and the Raman laser includes an original ring of laser fibers within the probe; wherein the probe includes a second ring including a plurality of lasers fibers at an angular incidence that expands and contracts with the original ring of laser fibers expand proportional to the movement of the axicon, and as the second ring expands and contracts, the angle of incidence decreases and increases, respectively; wherein the second ring of lasers provide greater intensity of the Raman signal by converging the path travelled by both rings of lasers on the same spot, and giving a stronger signal and allowing Raman laser to probe deeper into the region of interest; a frequency-offset Raman spectroscopy system with the Inverse Spatially Offset Raman Spectroscopy system, wherein the frequency-offset Raman spectroscopy system includes different excitation frequencies and changing the frequency based on the optical properties of the region of interest after gathering spectra of every type of tissue, the code would work with the Raman Spectroscopy software to change the frequency; a diode sheet at the collection end of the probe with a hole in the middle, wherein the diode sheet reflects scattering signals back into the region of interest and provide a better signal for a spectrometer; wherein the XY plotter controls the movement of the probe with a plurality of motors and a plurality of sensors to actively communicate with the XY plotter regarding the probe's distance from the region of interest; wherein the plurality of motors and the plurality of sensors communicate data regarding how far away probe is from the region on interest being scanned; wherein the plurality of motors comprise a first motor, a second motor, and a third motor; wherein the first motor is positioned on a vertical track and at the end of a horizontal track; the second motor moves the probe horizontally; the third motor moves the probe along a Z-axis; and a sensor operably coupled with the XY plotter to indicate how far the probe is away from the region of interest; and the Raman Spectroscopy software comprising: taking a Pt derivative from each spectra, storing each spectra data as a list with name of tissue, and creating a library with 'list' of tissues and each 'list' has a 'key'; and takes the files from library and conducting the following: Normalizing and taking the derivative for Math Adjustments; and Comparing a new graph to the library and if it matches, then assigning a letter, which assigns a numeric value; iii, a basic diagnostic including repeating for every spectra it finds in the folder and arranges the 'list' (array) in matrix shape of choice; scaling the value in a 0-1 scale with each 'key' in the matrix, which is used for black and white images; detecting cancer including looking at the designated cell value in all the files, then the value is switched to a 0-1 scale; putting every new value is in a list; and then resizing to fit the matrix (dimensions of scanned area); and converting the matrix to an image using an RGB multiplication tool.

\* \* \* \* \*